US009155861B2

(12) United States Patent
Hetke et al.

(10) Patent No.: US 9,155,861 B2
(45) Date of Patent: Oct. 13, 2015

(54) NEURAL DRUG DELIVERY SYSTEM WITH FLUIDIC THREADS

(75) Inventors: Jamille F. Hetke, Brooklyn, MI (US); Daryl R. Kipke, Dexter, MI (US); Rio J. Vetter, Ypsilanti, MI (US)

(73) Assignee: NeuroNexus Technologies, Inc., Ann Arbor, MI (US)

( * ) Notice: Subject to any disclaimer, the term of this patent is extended or adjusted under 35 U.S.C. 154(b) by 971 days.

(21) Appl. No.: 13/236,973

(22) Filed: Sep. 20, 2011

(65) Prior Publication Data
US 2012/0078188 A1  Mar. 29, 2012

Related U.S. Application Data (60) Provisional application No. 61/384,466, filed on Sep. 20, 2010.

(51) Int. Cl.
*A61M 25/00* (2006.01)

(52) U.S. Cl.
CPC ..... *A61M 25/007* (2013.01); *A61M 2025/0058* (2013.01); *A61M 2210/1003* (2013.01)

(58) Field of Classification Search
CPC .................. A61M 25/007; A61M 2210/1003; A61M 2025/0058
USPC .................. 604/20, 21, 66, 173, 890.1, 891.1
See application file for complete search history.

(56) References Cited

U.S. PATENT DOCUMENTS

| | | | |
|---|---|---|---|
| 3,847,687 A | 11/1974 | Davidsohn et al. |
| 3,921,916 A | 11/1975 | Bassous |
| 4,141,365 A | 2/1979 | Fischell et al. |
| 4,166,469 A | 9/1979 | Littleford |
| 4,306,562 A | 12/1981 | Osborne |
| 4,455,192 A | 6/1984 | Tamai |
| 4,461,304 A | 7/1984 | Kuperstein |
| 4,465,482 A | 8/1984 | Tittel |

(Continued)

FOREIGN PATENT DOCUMENTS

| | | |
|---|---|---|
| WO | 0112115 | 2/2001 |
| WO | 0236002 | 5/2002 |

(Continued)

OTHER PUBLICATIONS

Application No. PCT/IB06/53700, International Search Report mailed Nov. 21, 2008.
Application No. PCT/IB10/53250, International Search Report mailed Oct. 4, 2010.
Application No. PCT/US04/35030, International Search Report mailed Feb. 21, 2005.
Application No. PCT/US06/23139, International Search Report mailed Aug. 2, 2007.

(Continued)

*Primary Examiner* — Imani Hayman
(74) *Attorney, Agent, or Firm* — Michael F. Scalise (57) ABSTRACT

A neural drug delivery system with fluidic threads implantable into tissue, including: a plurality of fluid delivery conduits configured to transport fluid and having an array of fluid delivery ports through which the fluid is selectively released; a plurality of port gates each including a mesh structure coupled to a corresponding fluid delivery port and coated with an electroactive polymer; a voltage source providing a conductive signal; and an interconnect network that carries the conductive signal to the port gates. In response of the electroactive polymer to the conductive signal, each port gate is selectively operable between a closed mode that prevents transfer of fluid through its corresponding fluid delivery port to the tissue, and an open mode that allows transfer of the fluid through its corresponding fluid delivery port to the tissue.

27 Claims, 8 Drawing Sheets

(56) References Cited

U.S. PATENT DOCUMENTS

| | | |
|---|---|---|
| 4,762,135 A | 8/1988 | van der Puije et al. |
| 4,886,065 A | 12/1989 | Collins, Jr. |
| 4,904,237 A | 2/1990 | Janese |
| 5,108,819 A | 4/1992 | Heller et al. |
| 5,180,376 A | 1/1993 | Fischell |
| 5,207,709 A | 5/1993 | Picha |
| 5,215,088 A | 6/1993 | Normann et al. |
| 5,308,442 A | 5/1994 | Taub et al. |
| 5,322,064 A | 6/1994 | Lundquist |
| 5,385,635 A | 1/1995 | O'Neill |
| 5,390,671 A | 2/1995 | Lord et al. |
| 5,409,469 A | 4/1995 | Schaerf |
| 5,496,360 A | 3/1996 | Hoffmann et al. |
| 5,515,848 A | 5/1996 | Corbett, III et al. |
| 5,524,338 A | 6/1996 | Martyniuk et al. |
| 5,573,520 A | 11/1996 | Schwartz et al. |
| 5,585,827 A | 12/1996 | Murakami |
| 5,588,597 A | 12/1996 | Reinecke et al. |
| 5,720,099 A | 2/1998 | Parker et al. |
| 5,744,958 A | 4/1998 | Werne |
| 5,800,535 A | 9/1998 | Howard, III |
| 5,843,150 A | 12/1998 | Dreessen et al. |
| 5,927,277 A | 7/1999 | Baudino et al. |
| 5,938,694 A | 8/1999 | Jaraczewski et al. |
| 5,975,085 A | 11/1999 | Rise |
| 5,989,445 A | 11/1999 | Wise et al. |
| 5,992,769 A | 11/1999 | Wise et al. |
| 6,006,124 A | 12/1999 | Fischell et al. |
| 6,016,449 A | 1/2000 | Fischell et al. |
| 6,044,304 A | 3/2000 | Baudino |
| 6,132,456 A | 10/2000 | Sommer et al. |
| 6,181,569 B1 | 1/2001 | Chakravorty |
| 6,205,361 B1 | 3/2001 | Kuzma et al. |
| 6,228,111 B1 | 5/2001 | Törmälä et al. |
| 6,324,433 B1 | 11/2001 | Errico |
| 6,325,797 B1 | 12/2001 | Stewart et al. |
| 6,374,143 B1 | 4/2002 | Berrang et al. |
| 6,430,443 B1 | 8/2002 | Karell |
| 6,600,231 B2 | 7/2003 | Tominaga |
| 6,618,623 B1 | 9/2003 | Pless et al. |
| 6,829,498 B2 | 12/2004 | Kipke et al. |
| 6,834,200 B2 | 12/2004 | Moxon et al. |
| 6,878,643 B2 | 4/2005 | Krulevitch et al. |
| 7,004,948 B1 | 2/2006 | Pianca et al. |
| 7,006,859 B1 | 2/2006 | Osorio et al. |
| 7,010,356 B2 | 3/2006 | Jog et al. |
| 7,011,680 B2 | 3/2006 | Alt |
| 7,089,059 B1 | 8/2006 | Pless |
| 7,181,288 B1 | 2/2007 | Rezai et al. |
| 7,343,205 B1 | 3/2008 | Pianca et al. |
| 7,548,775 B2 | 6/2009 | Kipke et al. |
| 7,871,707 B2 | 1/2011 | Laude et al. |
| 7,914,842 B1 | 3/2011 | Greenberg et al. |
| 7,941,202 B2 | 5/2011 | Hetke et al. |
| 2001/0049499 A1 | 12/2001 | Lui et al. |
| 2002/0052610 A1 | 5/2002 | Skakoon et al. |
| 2002/0111601 A1* | 8/2002 | Thompson ............... 604/514 |
| 2002/0183817 A1 | 12/2002 | Van Venrooij et al. |
| 2002/0198446 A1 | 12/2002 | Hill et al. |
| 2003/0093129 A1 | 5/2003 | Nicolelis et al. |
| 2003/0100823 A1 | 5/2003 | Kipke et al. |
| 2003/0114906 A1 | 6/2003 | Booker et al. |
| 2003/0187461 A1 | 10/2003 | Chin |
| 2004/0006264 A1 | 1/2004 | Mojarradi et al. |
| 2004/0102828 A1 | 5/2004 | Lowry et al. |
| 2004/0106169 A1 | 6/2004 | Evans |
| 2004/0199235 A1 | 10/2004 | Younis |
| 2005/0004627 A1 | 1/2005 | Gibson et al. |
| 2005/0021116 A1 | 1/2005 | He et al. |
| 2005/0021117 A1 | 1/2005 | He et al. |
| 2005/0137647 A1 | 6/2005 | Wallace et al. |
| 2005/0222647 A1 | 10/2005 | Wahlstrand et al. |
| 2006/0122677 A1 | 6/2006 | Vardiman |
| 2006/0138371 A1 | 6/2006 | Garnier |
| 2006/0173263 A1 | 8/2006 | He et al. |
| 2006/0247749 A1 | 11/2006 | Colvin |
| 2006/0258951 A1 | 11/2006 | Bleich et al. |
| 2006/0276866 A1 | 12/2006 | Mccreery |
| 2006/0282014 A1 | 12/2006 | Kipke et al. |
| 2007/0073130 A1 | 3/2007 | Finch et al. |
| 2007/0123765 A1 | 5/2007 | Hetke et al. |
| 2007/0135885 A1 | 6/2007 | Risi |
| 2008/0132970 A1 | 6/2008 | Barolat |
| 2008/0208283 A1 | 8/2008 | Vetter et al. |
| 2008/0255439 A1 | 10/2008 | Tang et al. |
| 2008/0262584 A1 | 10/2008 | Bottomley et al. |
| 2009/0099555 A1 | 4/2009 | Viohl et al. |
| 2009/0102068 A1 | 4/2009 | Pellinen et al. |
| 2009/0118806 A1 | 5/2009 | Vetter et al. |
| 2009/0132042 A1 | 5/2009 | Hetke et al. |
| 2009/0149934 A1 | 6/2009 | Ameri et al. |
| 2009/0171421 A1 | 7/2009 | Atalar et al. |
| 2009/0187196 A1 | 7/2009 | Vetter |
| 2009/0234426 A1 | 9/2009 | Pellinen et al. |
| 2009/0240314 A1 | 9/2009 | Kong et al. |
| 2009/0248118 A1 | 10/2009 | Bradley et al. |
| 2009/0253977 A1 | 10/2009 | Kipke et al. |
| 2009/0299167 A1 | 12/2009 | Seymour |
| 2009/0312770 A1 | 12/2009 | Kozai et al. |
| 2010/0030298 A1 | 2/2010 | Martens et al. |
| 2010/0145216 A1 | 6/2010 | He et al. |
| 2010/0145422 A1 | 6/2010 | Seymour et al. |
| 2011/0093052 A1 | 4/2011 | Anderson et al. |
| 2011/0154655 A1 | 6/2011 | Hetke et al. |

FOREIGN PATENT DOCUMENTS

| | | |
|---|---|---|
| WO | 0241666 | 5/2002 |
| WO | 02096482 | 12/2002 |
| WO | 2005039696 A | 5/2005 |
| WO | 2006138358 A | 12/2006 |
| WO | 2007042999 A | 4/2007 |
| WO | 2007089738 A | 8/2007 |
| WO | 2008011721 A | 1/2008 |
| WO | 2008038208 A | 4/2008 |
| WO | 2008072125 A | 6/2008 |
| WO | 2008109298 A | 9/2008 |
| WO | 2009052423 A | 4/2009 |
| WO | 2009052425 A | 4/2009 |
| WO | 2010057095 A | 5/2010 |
| WO | 2011010257 A | 1/2011 |
| WO | 2011046665 A | 4/2011 |

OTHER PUBLICATIONS

Application No. PCT/US07/02465, International Search Report mailed Feb. 13, 2008.

Application No. PCT/US08/55025, International Search Report and Written Opinion mailed Oct. 27, 2008.

Application No. PCT/US08/80364, International Search Report and Written Opinion mailed Dec. 16, 2008.

Application No. PCT/US08/80366, International Search Report and Written Opinion mailed Dec. 10, 2008.

Application No. PCT/US09/64591, International Search Report and Written Opinion mailed Jul. 21, 2010.

Application No. PCT/US10/44167, International Search Report and Written Opinion mailed Sep. 27, 2010.

Kaplan et al., "A Novel Fabrication Method of Capillary Tubes on Quartz for Chemical Analysis Applications," IEEE Proc., Micro Electro Mech Systems, Jan. 25-28, 1994.

Lin et al., "Silicon Processed Microneedles," IEEE J. Micro. Electro. Mech. Sys, vol. 8, No. 1 (1999) 78-84 (7 pages).

Seymour et al., "Neural probe design for reduced tissue encapsulation in CNS," Biomaterials 28 (2007) 3594-3607, Apr. 5, 2007 (14 pages).

Seymour et al., "The insulation performance of reactive parylene films in electronic devices," Biomaterials (2009) 6158-6167, Aug. 22, 2009 (10 pages).

* cited by examiner

|  | EXAMPLES |
|---|---|
| CONDUIT SPECIFICATION | |
| Conduit Diameter | 1 mm, 600 μm |
| Insertable length | ≥ 3 cm |
| # conduits | 1, 8 |
| Implant Method | stylet |
| FLOW SPECIFICATION | |
| # of ports/conduit | 1, 8 |
| Port spacing | 2 mm |
| Port diameter | 250 μm |
| Applied Pressure | 2 – 15 PSI |
| Flow rate | 0.5 – 10 μL/min |
| Leakage | <1 nL/min |
| MESH SPECIFICATION | |
| Crossbar width | 5, 10, 15 μm |
| Crossbar gap | 5, 10, 15 μm |
| Crossbar thickness | 2, 5, 10, 15, 20 μm |
| COATING SPECIFICATION | |
| Composition | PPy(Cl), PPy(ClO$_4$), PPy (CF$_3$SO$_3$), PPy (PF$_6$) |
| Thickness | 2, 5, 10 μm |
| ELECTRODE SPECIFICATION | |
| # of sites | 3, 8 |
| Site spacing | 2 mm |
| Site shape | annular, elliptical |
| Site material | Au, Pt, Ir, PPy |
| Site impedance | 500 – 1000 kOhms |

FIG. 9

FIG. 10

NEURAL DRUG DELIVERY SYSTEM WITH FLUIDIC THREADS

CROSS-REFERENCE TO RELATED APPLICATIONS

This application claims the benefit of U.S. Provisional Application No. 61/384,466 filed 20 Sep. 2010, which is hereby incorporated in its entirety by this reference.

TECHNICAL FIELD

This invention relates generally to the medical field, and more specifically to an improved neural drug delivery system in the oncology field.

BACKGROUND

According to the American Cancer Society, in 2009, there were approximately 20,000 deaths in the United States from malignant brain tumors. The most aggressive of these tumors, Grade III and IV malignant glioblastoma multiforme (GBM) is particularly resistant to treatment. A patient receiving a diagnosis of a GBM will most likely die within just a year or two; the median survival rate is about 12 months, regardless of treatment. Today, the stark finding is that treatment options are limited and there is no obvious silver bullet on the horizon. However, amidst the complexities of the disease and the ongoing efforts poured into current surgical, radiation, and chemotherapy treatments, there is a growing technical, and clinical rationale for pursuing targeted drug delivery directly to brain tumors as a next-generation therapy. In this approach, the objective is to deliver the right therapeutic agent (e.g., conventional small molecule chemotherapy drug, large molecule biologic drug, nanoparticle, or perhaps even virus vector) to the correct brain region, at the most efficacious times and at the most efficacious dosage, all while not damaging normal brain tissue and maintaining patient safety and quality of life. This is a difficult, largely unsolved problem due to the critical intrinsic complexities of the tumor-brain system and interfacing with it, including complex and highly variable tumor morphology, composition, and mass transport, and complex technologies required for sophisticated implantable drug delivery devices.

One of the promising new treatments is referred to as convection-enhanced delivery (CED). In this approach, cancer-fighting drugs are directly infused under pressure into the tumor using an implanted catheter. CED is attractive because (1) it bypasses the blood-brain-barrier (BBB) and the systemic vascular system to deliver chemotherapeutic agents directly into the interstitial space of the parenchyma and (2) it uses external pressure to supplement the slow mass transport achieved by diffusion and achieve a degree of infusion control. However, a fundamental problem with clinical CED to-date is that current catheters and injection methods have not been sufficient to overcome the critical intrinsic complexities of targeted drug delivery to tumors (such as complex tumor morphologies, and non-homogenous and dynamic hydrostatic and mass transport characteristics), nor to address the need for precise control of drug concentrations over time (days) and space (centimeters) in tumor, brain, and interstitial volumes. Quite simply, CED drug delivery technologies have not kept pace with CED application requirements.

Thus, there is a need in the medicine field to create an improved neural drug delivery system. This invention provides such an improved neural drug delivery system.

DESCRIPTION OF THE PREFERRED EMBODIMENTS

The following description of preferred embodiments of the invention is not intended to limit the invention to these preferred embodiments, but rather to enable any person skilled in the art to make and use this invention.

Components of the Neural Drug Delivery System

Figure 1A:
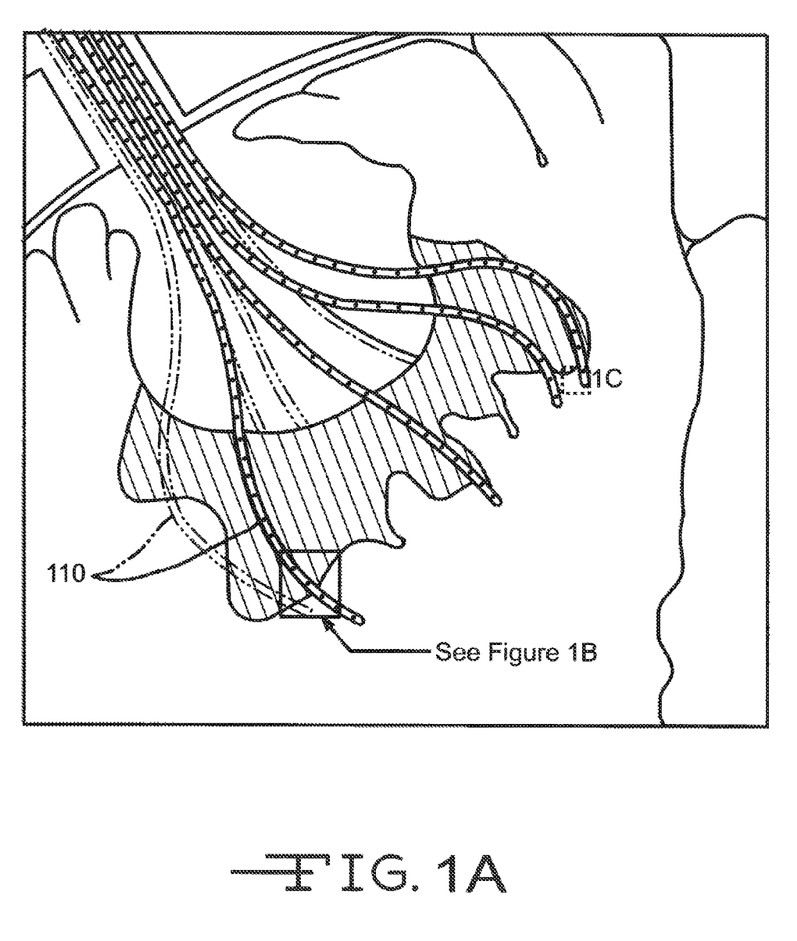
FIGS. 1A-1D and 2 are schematics of the neural drug delivery system of a preferred embodiment implanted in tissue.
Figure 1B:
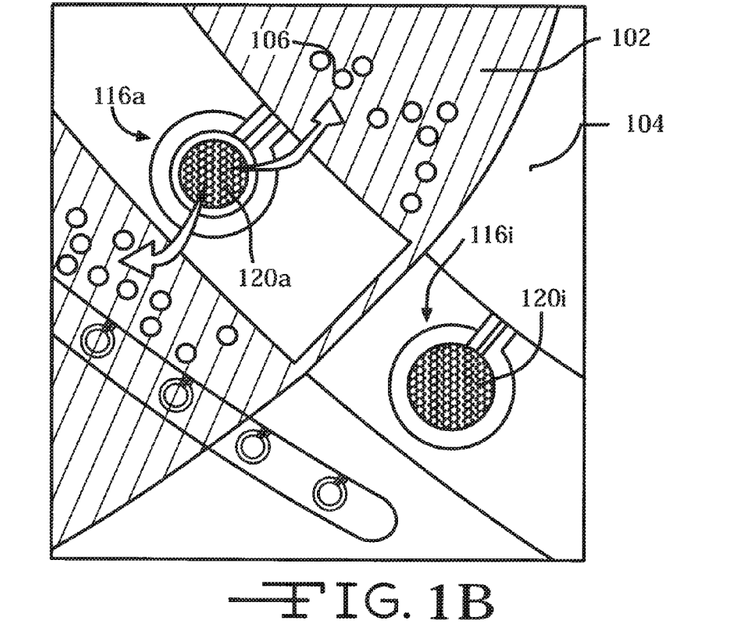
Figures 1C, 1D:
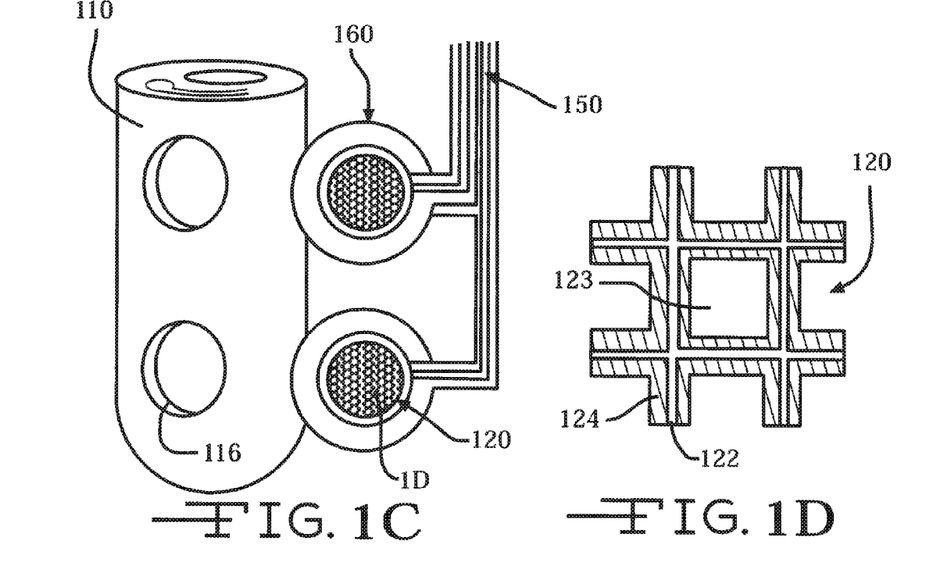
Figure 2:
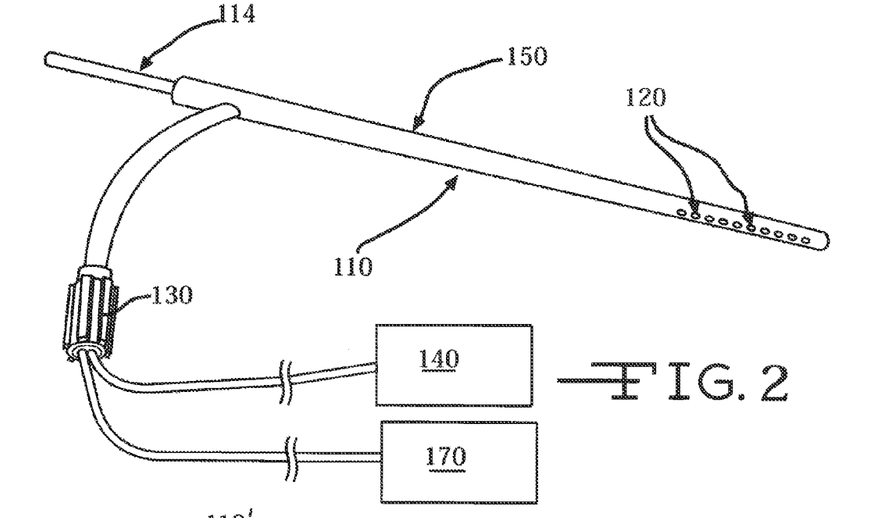

As shown in FIGS. 1-3, the neural drug delivery system 100 of a preferred embodiment includes: a plurality of elongated fluid delivery conduits 110, or "fluidic threads", that are implantable into tissue and configured to transport fluid 106 in which each of at least a portion of the conduits defines an array of fluid delivery ports 116 through which fluid is selectively released to the tissue; a plurality of port gates 120 each including a thin-film mesh structure 122 that is coupled to a corresponding fluid delivery port 116 and at least partially coated with an electroactive polymer 124, in which each port gate is selectively operable between a closed mode and an open mode in response of the electroactive polymer 124 to a conductive signal; a voltage source 140 that provides the conductive signal to the plurality of port gates 120; and an interconnect network 150, coupled to the voltage source and to the plurality of port gates, that carries the conductive signal from the voltage source to each of the plurality of port gates. In the closed mode 126 of a port gate shown in FIG. 4, the port gate prevents transfer of the fluid through its corresponding fluid delivery port to the tissue. In the open mode 128 of a port gate shown in FIG. 6, the port gate allows transfer of the fluid through its corresponding fluid delivery port to the tissue. The plurality of port gates 120 preferably includes a first portion of port gates that is operable between the closed and open modes independently of a second portion of port gates. At least a portion of the fluidic threads may further include an array of electrode sites suitable for recording, stimulation, and/or impedance measurements, such as for enabling feedback control of drug delivery and relative localization of drug to the targeted tissue, or other applications.

The neural drug delivery system 100 with fluidic threads preferably provides highly adjustable pressure-driven drug infusion at selectable discrete locations, particularly for the treatment of cancer. A coarse level of drug coverage control is preferably achieved by determining the number of fluidic threads implanted in the tissue and their position in and around a tumor. An additional, finer level of drug coverage control is preferably achieved by adjusting infusion pressure amplitude and waveform, and/or by selectively operating a desired portion of port gates 120 between their closed and open modes. Further control of drug delivery to tissue may be achieved by selectively operating the port gates 120 in one or more gradient open modes, that allow transfer of the fluid through its corresponding port at any one of a range of flow rates (i.e., gates are partway open). The fine control of drug delivery is useful, for example, to optimize drug delivery and treatment to unique terrain of a particular tumor while avoiding drug delivery to non-cancerous tissue and reducing adverse effects on healthy tissue.

In another embodiment, the neural drug delivery system may include stimulation electrode sites, and additionally and/or alternatively be used for electrochemotherapy, which uses electric fields to enhance the cytotoxicity level of standard chemotherapeutic treatment of tumors. Applying an electric field to tissue increases cell permeability in a process called electroporation, thereby increasing the efficacy of chemotherapy treatment.

In one exemplary application, the neural drug delivery system 100 enables a means for precise, scalable, and programmable direct delivery of chemotherapeutic agents to brain tumors over time. The neural drug delivery system preferably supports clinical therapy for brain tumors, but may be used for any suitable type of fluid delivery in other neural tissue, or any suitable body tissue or other substance. Additionally, the actuation system of the port gates may be used in other applications that employ gating of a small fluidic port, in other drug delivery devices (e.g., any suitable type of catheter) or other suitable applications that require precise microfluidic flow control. At the system level, the neural drug delivery system is innovative in terms of, for example, (1) achieving individually addressable gradient flow control across an array of fluid ports 116 to improve controlled drug delivery; (2) integrated sensing of relative location and local tissue properties using neural recording and measuring local tissue impedance; (3) use of clinical-grade materials and components to increase clinical and commercial feasibility.

The plurality of fluid delivery conduits 110, also referred to herein as "fluidic threads", function to transport a fluid such as chemotherapy drug treatment or any suitable fluid within the system. As shown in FIG. 1, distal portions of the plurality of fluidic threads 110 are preferably implanted into a particular targeted location such as in a brain tumor or any suitable tissue. The fluidic threads are preferably flexible, but a fluidic thread may include at least a portion that has any suitable amount of rigidity. Proximal portions of the fluidic threads are preferably externalized outside the cranium and connected to an external controllable infusion pump, drug reservoir, and/or control instrumentation or other device. Outside the body, the proximal portions of the fluidic threads are preferably clustered, but alternatively each fluidic thread may be individually connected to a corresponding infusion pump, drug reservoir, and/or control instrumentation or other device. All of the fluidic threads may transport the same fluid, or different fluidic threads may be coupled to different devices and transport different fluids.

Figure 3A:
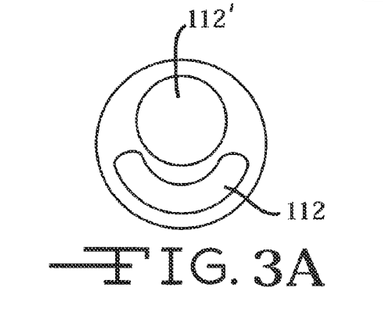
FIGS. 3A-3C are variations of the fluid delivery conduits in the neural drug delivery system of a preferred embodiment.
Figure 3B:
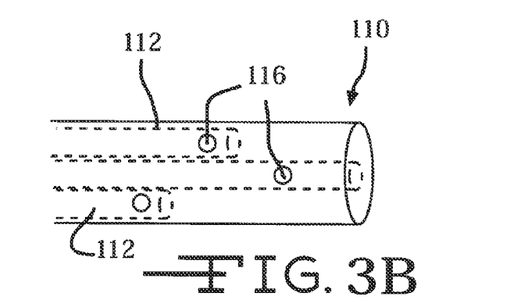
Figure 3C:
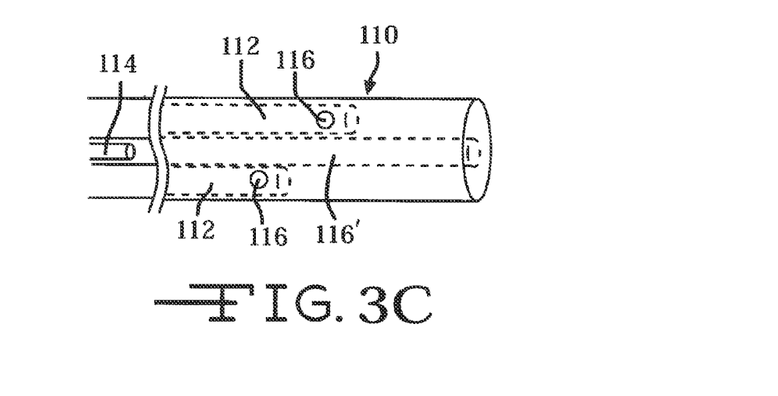

As shown in FIG. 3A, the fluidic threads 110 each preferably includes at least one lumen 112 such that the .fluidic threads transport the fluid with the lumen, and as shown in FIGS. 3B and 3C, a fluidic thread may include multiple lumens 112 that transport multiple fluids. For example, a fluidic thread may include two lumens each transporting a different fluid, where a first lumen carrying a first fluid is in fluidic communication with a first portion of the ports 116 and a second lumen carrying a second fluid is in fluidic communication with a second portion of the ports 116. The lumen 112 is preferably arcuate such that it extends at least partially circumferentially along a side wall of the fluidic thread, but may be lune-shaped, elliptical, circular, or any suitable shape. The lumen 112 may be pressurized by an infusion pump 170 or other source to help facilitate fluid flow through a port 116 when its corresponding port gate 120 is in the open mode. For example, the internal pressure of the fluidic thread may be set or modulated between approximately 2-15 psi, but may alternatively be set or modulated to any suitable pressure level. However, some or all of the fluidic threads may additionally and/or alternatively include receptacles that are pre-filled with the fluid prior to implantation of the fluidic threads, with each receptacle being coupled to a corresponding port gate. In another alternative, some or all of the fluidic threads may be impregnated with a drug or another substance that is released into and absorbed by tissue over time. Any one fluidic thread may also have a combination of one or more lumens that transport a fluid from an external device, one or more fluid receptacles, and/or be impregnated with a time-released substance. In these alternative versions, the fluidic threads may be solid, and the receptacles and/or impregnations may or may not be coupled to a corresponding port that regulates transfer of the fluid to the target tissue.

As shown in FIG. 2, the fluidic threads 110 may include a passageway that receives a removable, steerable stylet 114. The fluidic threads are preferably positioned in targeted tissue by inserting the stylet 114 into a lumen or other passageway 112' of a fluidic thread, manipulating the stylet 114 to control the position of the fluidic thread, and removing the stylet 114 from the passageway of the fluidic thread. The stylet 114 may be flexible and/or jointed, and steerable through manual manipulation, cables, or any suitable control system. Alternatively, the stylet may couple to the fluidic thread in any suitable manner, and/or the stylet may be resorabable into the body after the fluidic thread is positioned. During implantation, the fluidic threads may be strategically positioned and manipulated to avoid nontargeted tissue as much as possible, such as to reduce unnecessary tissue damage.

At least a portion of the fluidic threads 110 preferably defines an array of fluid. delivery ports 116 through which transfer of the fluid from the fluidic thread to the target tissue is facilitated. As shown in FIGS. 1-3, the fluid delivery ports 116 are preferably distributed along the length of the fluidic thread, and may be additionally and/or alternatively located on a tip of the fluidic thread. The array of ports may be distributed longitudinally along and/or circumferentially around the fluidic thread. The array of ports may be arranged in a regular pattern (e.g., rectangular or triangular) or in an irregular pattern. The ports are preferably elliptical (including circular), but may be rectangular, square, or any suitable shape. In one embodiment, each fluidic thread 110 includes eight fluid delivery ports, but may alternatively include any suitable number of ports. The number and size of the ports may vary depending on the application (e.g., type of surrounding tissue) or the type of fluid (e.g., viscosity).

As shown in FIGS. 1B and 1C, in some embodiments the fluidic threads 110 may include an array of sensors and/or electrode sites 160 along their length or tip. The array of sensors and/or electrode sites (e.g. recording or stimulation electrode sites) is preferably arranged near one or more fluid delivery ports 116. In particular, as best shown in FIG. 1B, the sensors and/or electrode sites 160 may be annular structures positioned around the perimeter of a fluid delivery port, and/or integrated with the fluid delivery port to produce a multi-modal, multichannel array capable of simultaneous drug delivery and recording, stimulation, and/or impedance setting. in alternative variations, the sensors and/or electrode sites may be any suitable shape. Furthermore, the sensors and/or electrode sites may alternatively be separate structures independent of the ports and/or fluidic threads. The array of sensors and/or electrode sites preferably facilitate local neural recording and/or tissue impedance sensing that enable feedback control of fluid delivery and relative localization. Furthermore, stimulation electrode sites may be used to apply a high voltage electric field as part of electrochemotherapy treatment. For example, the fluidic threads of the neural drug delivery system may include stimulation electrodes that can be used to apply an electric field to target tissue that is deeper and less accessible, where the electric field is highly customizable and adjustable based on the tissue environment. In one embodiment, each fluidic thread 110 includes eight electrode sites, but may alternatively include any suitable number of sensors or electrode sites.

Figure 4:
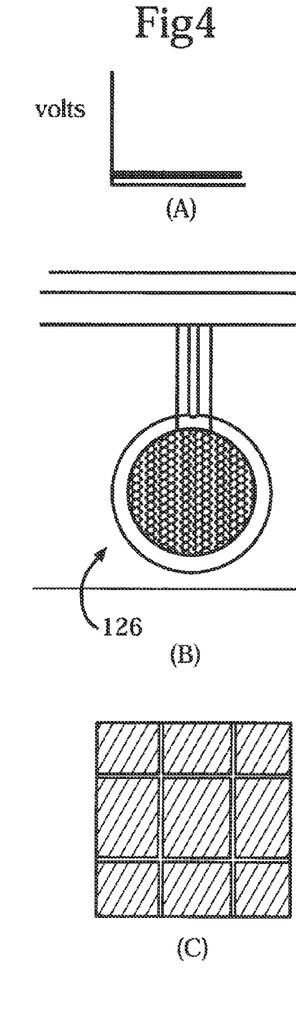
FIGS. 4A-4C are schematics of the relative conductive signal input, overall view, and detailed view, respectively, of the port gate in the closed mode in the neural drug delivery system of a preferred embodiment.
Figure 5:
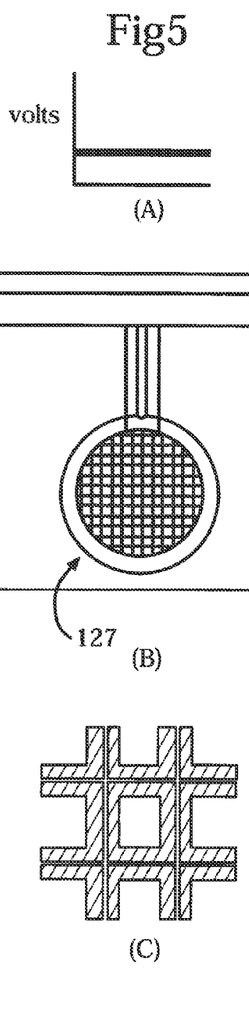
FIGS. 5A-5C are schematics of the relative conductive signal input, overall view, and detailed view, respectively, of the port gate in a gradient open mode in the neural drug delivery system of a preferred embodiment.
Figure 6:
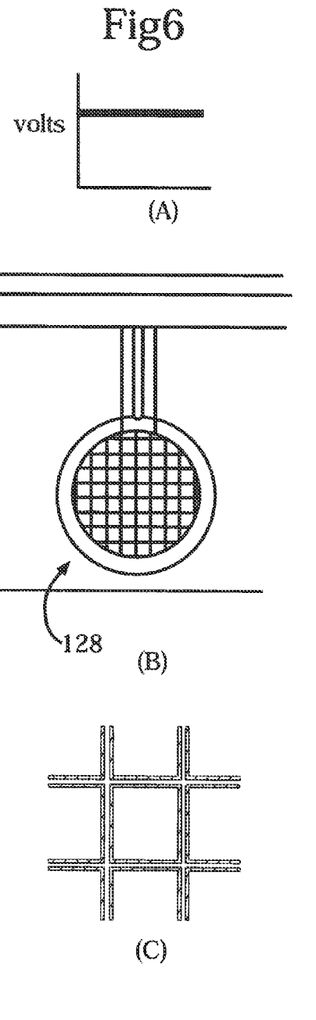
FIGS. 6A-6C are schematics of the relative conductive signal input, overall view, and detailed view, respectively, of the port gate in the open mode in the neural drug delivery system of a preferred embodiment.

As shown in FIG. 1, the port gates 120 of the neural delivery system function as controllable valves that provide control over when and where the fluid is administered to neighboring tissue, by selectively regulating the transfer of the fluid through some or all of the ports. As shown in FIGS. 4-6, each port gate is preferably coupled to a corresponding port, and is selectively operable between a closed mode 126 and an open mode 128 and in some embodiments, one or more gradient open modes 127. In the closed mode 126, the port gate prevents transfer of the fluid through its corresponding port to the surrounding tissue. In the open mode 128, the port gates 120 allow transfer of the fluid through its corresponding port to the surrounding tissue. The port gates may further operate in gradient open modes 127 that allow any of a range of flow rates of fluid through the port. The gradient open modes are preferably provided by opening the port gate in partially open (or partially closed) configurations.

In a given application, some or all of the fluid delivery ports 116 may be "active " or "inactive" based on the activity of their corresponding port gates 120. An "active" port 116a may be considered to be a port whose corresponding port gate 120a is operated in the open mode at least some of the time. Conversely, an "inactive" port. 116i may be considered to be a port whose corresponding port gate 120i is never operated in the open mode, and is always in the closed mode As shown in FIG. 1, when the fluidic threads 110 are implanted in tissue such that a first portion of the fluidic threads is in target tissue 102 (such as a tumor) and a second portion of the fluidic threads is in nontargeted tissue 104 (such as healthy, non-cancerous tissue), the ports on the first portion of the fluidic threads may be active ports 116a since it is desirable to have fluid administered to target issue 102 at least some of the time, while the ports on the second portion of the fluidic threads may be inactive ports 116i since it is desirable to avoid adverse effects of the fluid administered. to nontargeted tissue 104.

Figure 9:
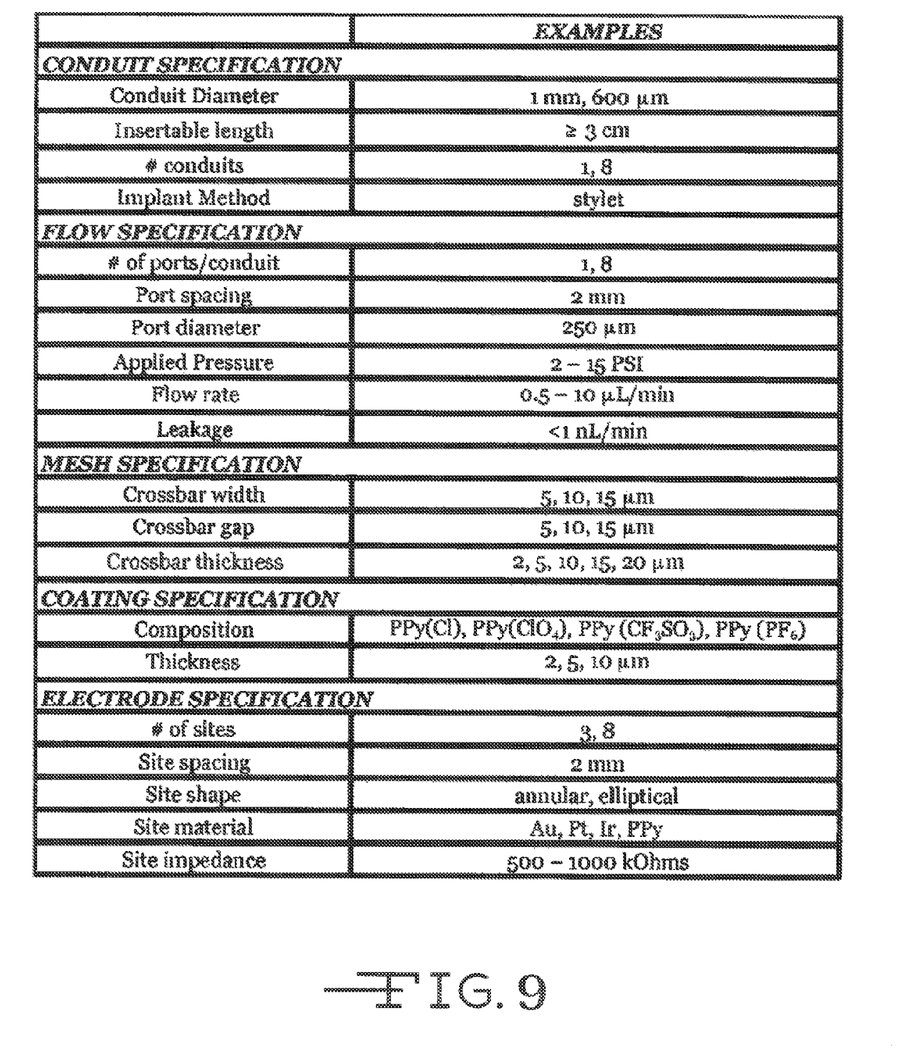
FIG. 9 is a table of example specifications of the neural drug delivery system of a preferred embodiment.

As shown in FIG. 1D, each port gate preferably includes a mesh structure 122 coupled to a corresponding port and an electroactive polymer coating 124 on the mesh structure that is manipulated with a conductive signal to induce the closed and open modes of the port gate. The mesh structure 122 is preferably a microfabricated thin-film metal mesh, and more preferably a gold mesh, although the mesh may alternatively include any suitable material. The mesh dimensions, including crossbar dimensions, mesh size, and number of gaps per mesh structure, may depend on the application and properties of the electroactive polymer. Crossbar thickness and width of the mesh structure are major contributors to the mechanical strength of the mesh structure, impacting its ability to withstand pressure, whereas the mesh gap size is directly related to flow rate in the open mode of the port gate and the ability of the polymer coating 124 to induce the closed mode 126 of the port gate. In one embodiment, each mesh structure has between 150 and 600 gaps or mesh holes 123. Dimensions and quantities may be chosen, for example, to show a reproducible 35% increase in thickness in the closed mode compared to the open mode. However, the mesh structure may have any suitable specifications, including but not limited to those shown in FIG. 9 of exemplary embodiments.

The electroactive polymer coating 124 on the mesh structure 122 is preferably a conjugated polymer that undergoes volume expansion or contraction when its oxidation or doping level is changed, thereby occluding or opening the mesh structure and inducing the closed or open modes, respectively. The doping level is preferably modulated by applying varying levels of conductive signal (e.g. voltage). Preferably, the polymer coating is a material that is stable in an expanded (mesh-occluding) state, so that the port gate is in its closed mode by default, without requiring power to maintain the port gate in the closed mode.

In a preferred embodiment, the coating 124 is an anion-transporting variation of polypyrrole (PPy). An anion-transporting variation of PPy may be developed by electropolymerizing the PPy in the presence of small anions, $ClO_4$, $BF_4$, or $PF_6$, or any suitable anion, as one ordinarily skilled in the art will know. In this preferred embodiment, the PPy coating 124 is stable in its oxidized and expanded state, meaning that a voltage must be actively applied to the PPy to retain the reduced and contracted state (this is due to oxygen doping and the polymer's electrochemical redox peak positions). Therefore, in this embodiment, as shown in FIG. 4, the port gates 120 preferably operate in the closed mode by default (e.g. zero or relatively low voltage) due to the oxidized and expanded PPy coating 124 occluding the mesh structure, requiring actuation only when the open or gradient open mode of the port gate is desirable (e.g., when in tumor tissue). As shown in FIG. 6, to induce the open mode 128 of the port gates 120, a voltage is preferably applied to the PPy coating 124 to cause the coating 124 to become reduced and contracted, thereby opening the mesh structure and allowing fluid transfer through the port. As shown in FIG. 5, to induce a gradient open mode 127 of the port gates 120, one of a range of voltages is preferably applied to the PPy coating 124 to cause the coating 124 to reduce and contract by a particular discrete amount dependent on the applied voltage amount, thereby partially opening the mesh structure by an amount corresponding to the applied voltage amount. In some embodiments, the port gates may be bimodal and operate between a closed mode 126 and solely one open mode; in other embodiments, the port gates may operate among a closed mode 126 and any suitable number of gradient open modes 127.

In a preferred embodiment, the anion-transporting PPy coating 124 may be one of three varieties of PPy: (1) PPy(Cl) gels, (2) $PPy(ClO_4)$ gels reaching approximately 43% strain, (3) the $PPy(CF_3SO_3)$ gels reaching approximately 19% strain, and (4) the $PPy(PF_6)$ reaching approximately 15% strain, or any variation reaching any suitable strain. In additional variations, the polymer properties of the coating on the port gates 120 may be tailored by adjusting the polymerization temperature, electrolyte concentration, and applied potential, among other parameters. As one example, one possible set of requirements for the port gates is that they exhibit leakage less than 1 nanoliter/minute in the closed mode, allow fluid flow of approximately 0.5 to 10 microliters/minute in the open mode (at least partially depending on applied fluidic pressure within the fluidic thread), and remain stable in physiological conditions (e.g., 37° C.). However, alternatively, the polymer coating 124 may alternatively be a cation-transporting type of PPy such as PPy(DBS), or any suitable kind of electroactive polymer that enables selective volume expansion or contraction to induce closed and open modes of the port gates. All the port gates preferably have the same kind of coating applied in an identical manner, but may alternatively have different coatings.

The voltage source 140 of the neural drug delivery system functions to provide a conductive signal that actuates the port gates 120 between the closed, open, and/or gradient open modes. The neural drug delivery system may include one voltage source, or multiple voltage sources. The voltage source 140 may be a battery, but may be any suitable kind of power source. The voltage source may be modulated to provide discrete levels of a conductive signal (e.g. 0.25 V, 0.5 V, 10V), or may be modulated to provide any level of conductive signal along a continuous range (e.g., between 0.0 V and 2.0 V). The voltage source is preferably configured to be located external to the body when the fluidic threads 110 are implanted in tissue, but may additionally and/or alternatively be configured to be located within the body when the fluidic threads are implanted in tissue.

Figure 7A:
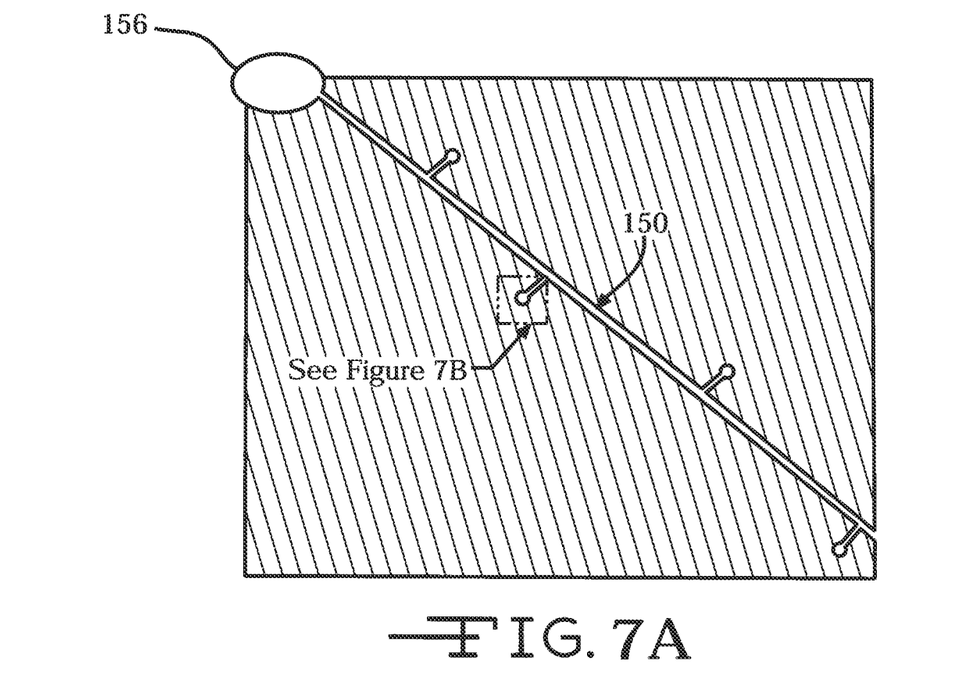
FIGS. 7A and 7B are schematics of the interconnect network, ports, and sensor and electrode array of the neural drug delivery system of a preferred embodiment.
Figure 7B:
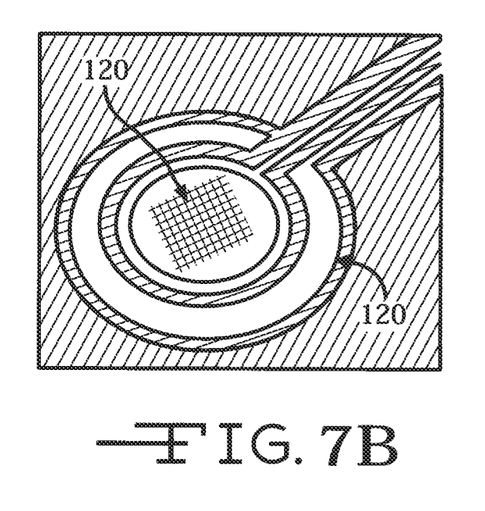
Figure 8A:
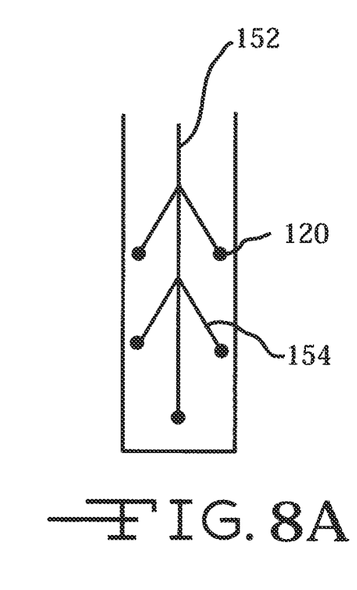
FIGS. 8A-8D are variations of the interconnect network of the neural drug delivery system of a preferred embodiment.
Figure 8B:
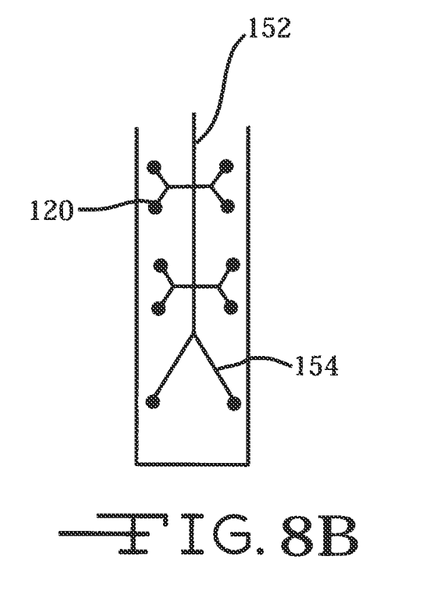
Figure 8C:
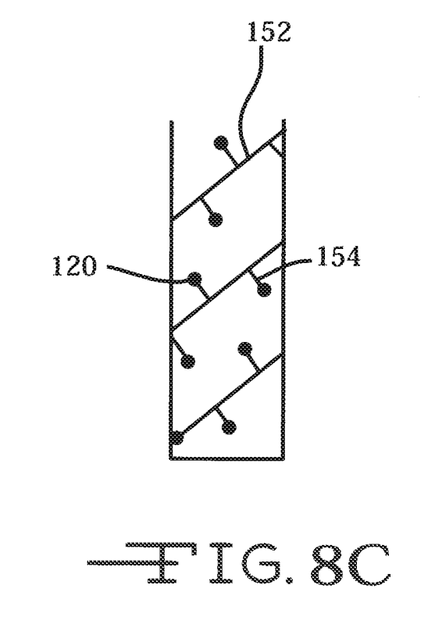
Figure 8D:
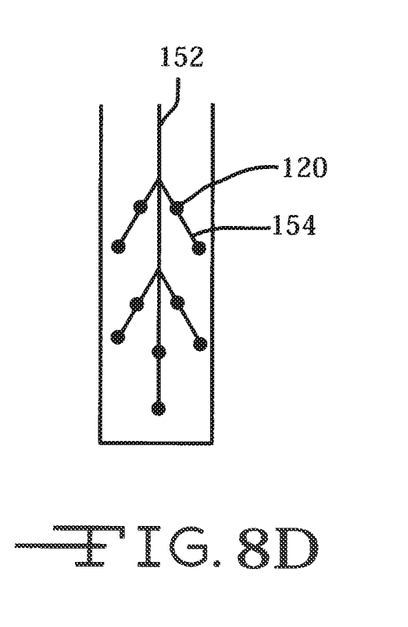

The interconnect network 150 of the neural drug delivery system functions to carry conductive signals to and from the port gates 120. The interconnect network 150 may additionally function to carry conductive signals to and from the array of sensors and/or electrodes, although the neural drug delivery system may include multiple interconnect networks, each for carrying different kinds of signals. As shown in FIG. 7, the interconnect network 150 is preferably a thin-film network that includes interconnect leads (such as a flexible ribbon cable) arranged along the fluidic threads and a bond pad region 156 preferably located on a proximal portion of the interconnect network, more preferably external to the cranium. As shown in FIGS. 7 and 8, the interconnect network 150 preferably includes a central spine 152 that carries interconnect leads along a fluidic thread, between the port gates 120 and/or electrode sites and the bond pad region. The central spine 152 may extend axially along the fluidic thread, but may travel along the fluidic thread in a curved or any suitable manner. The interconnect network preferably includes branches 154 that extend from the central spine 152 to one or more respective port gates 120, and these branches 154 may include one branching stage (FIGS. 7 and 8A) or multiple branching stages (FIG. 8B). The network may also include a spine and/or branches that wrap circumferentially around the fluidic thread, including helically (FIG. 8C). The ports and port gates are coupled to the branches on the network, preferably on the termination of the branch as in FIG. 8A, but alternatively and/or additionally on any length along a branch as in FIG. 8D. However, the network may have any suitable configuration that distributes the port and port gates for fluid transfer. Within the interconnect network, different portions of the port gates 120 are preferably operable independently of one another. In other words, a first portion of port gates may be actuated between the closed mode 126 and open mode 128 independently of a second portion of port gates. For example, actuation of the first portion of port gates into the open mode does not necessarily result in actuation of the second portion of port gates into the open mode. However, some of the port gates may be functionally grouped (e.g. multiple port gates along a single interconnect network branch) to have coupled actuation between the closed and open modes.

As shown in FIG. 2 the neural drug delivery system preferably further includes one or more connector assemblies 130 that couples the fluidic thread 110 to a fluidic source 170 and/or the voltage source 140, and/or to additional electronic subsystems. The additional electronic subsystems may include a printed circuit board (PCB) and connector pins that may be coupled to a control system, or may include a multiplexer and/or other suitable control instrumentation or electrical components for communicating with a control system. The system may include multiple connector assemblies, each coupled to a respective fluidic thread, or may include fewer connector assemblies than fluidic threads such that at least a portion of the connector assemblies couple to multiple fluidic threads.

Some embodiments of the neural drug delivery system may include internal gates located within the fluidic threads 110 that further regulate flow of drugs or other fluid within the fluidic threads. Such internal gates may be identical and operate similarly to the port gates, and/or may include any suitable kind of valve. For example, such internal gates may be useful in a fluidic thread having ports located along multiple branching stages, such that internal gates enable fluid delivery within the conduit 110 to only a portion of the ports. Furthermore, the neural drug delivery system may include features to reduce or eliminate reflux (backflow of the fluid into the fluidic threads), such as a step design cannula that is known by one ordinarily skilled in the art, or any suitable reflux-reducing feature.

Fabrication and Assembly of the Neural Drug Delivery System

At least some of the components of the neural drug delivery system 100 (including the fluidic thread, port gate, interconnect network and connector assembly) are preferably procured and/or fabricated separately before assembly. Particular specifications of the various components may be similar to those shown in FIG. 9 of exemplary embodiments, but the components may have any suitable specifications such as material type, compositions, and dimensions. In a preferred embodiment, the fluidic thread 110 is an extruded tube, such as an extruded tube made from a thermoplastic copolymer (e.g. CarboSil®, DSM PTG), or any material that provides suitable flexibility, biocompatibility, biostability, processability, and robustness or other suitable material. In a preferred embodiment, the extruded tubing has a diameter of approximately 600 μm and a length that allows for an insertable length (configured to be implanted in tissue) of at least 3 cm (more preferably 6 cm), but the tubing may have any suitable length and diameter. In another alternative variation, the extruded tube may be a polyimide tube, such as a polyimide tube having an outer diameter of 1 millimeter, or any suitable size. The tube is preferably prepared for assembly by sealing the distal end with epoxy and drilling one or more ports 116 in the side walls of the tube, but may be prepared in any suitable manner.

Figure 10:
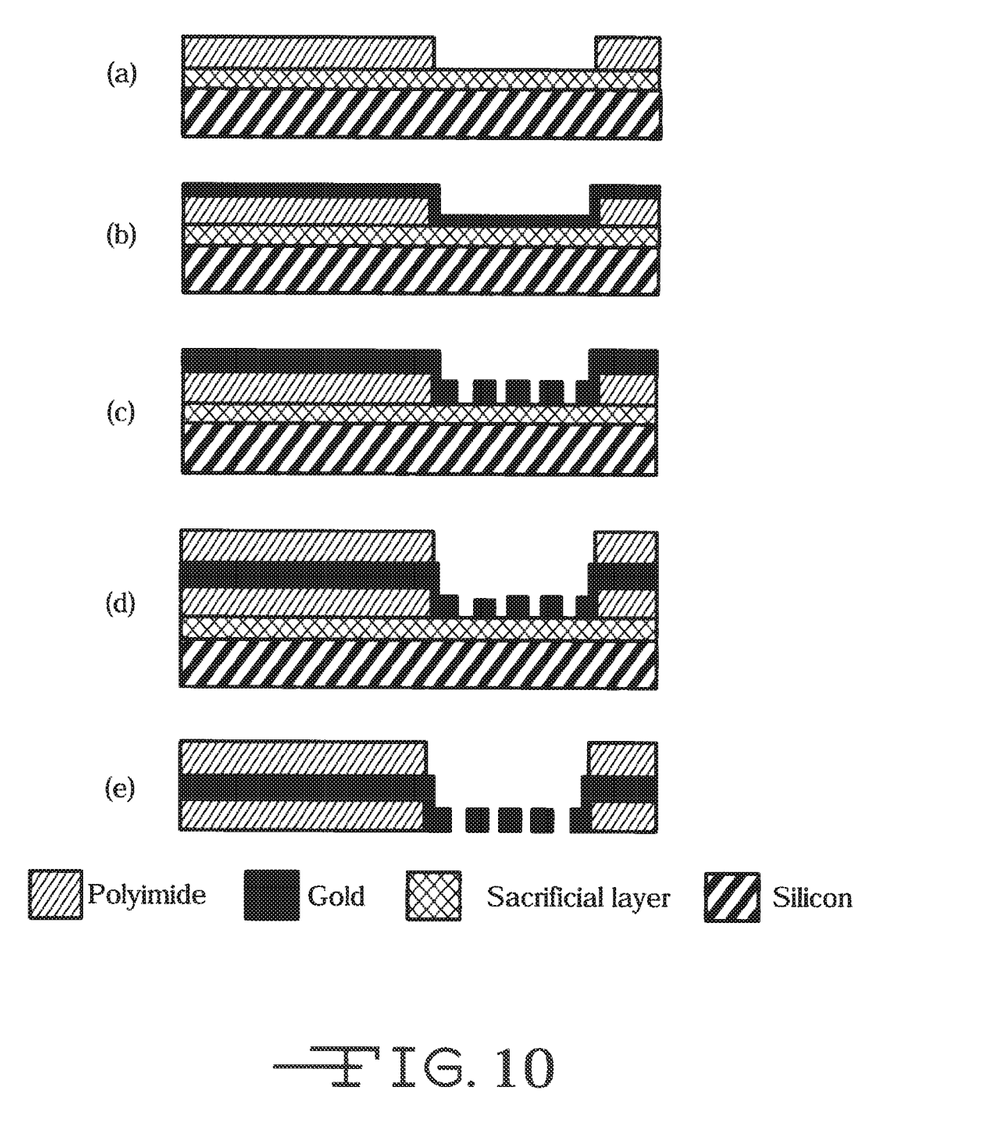
FIGS. 10A-10E are schematics of fabrication of a port gate in the neural drug delivery system of a preferred embodiment.

As shown in FIG. 10, in a preferred embodiment, fabrication of the port gate 120 begins with a silicon wafer as a substrate for the mesh structure. After a sacrificial layer has been deposited, approximately 3-5 μm of polyimide will be spun on, patterned, and etched (FIG. 10A). A Cr/Au seed layer will be deposited (FIG. 10B) and the Au mesh and interconnect layer will be electroplated to the chosen thickness through a patterned photoresist mask (FIG. 10C). After the photoresist is stripped and the Au seed layer is removed in the mesh structure gap areas, polyimide will be spun on (to a thickness of approximately 3-5 µm) and patterned to insulate the Au interconnect (FIG. 10D). The mesh structures 122 are then released by dissolving the sacrificial layer (FIG. 10E). The process requires at least 3 masks/lithography steps, and may incorporate any additional and/or alternative suitable materials in any step. In addition to polymer composition, there is a wide variety of parameters that can be adjusted, including concentration, dopant and temperature of deposition, and the composition and deposition conditions may be cooperatively altered to achieve any suitable specification for any suitable application. Any suitable materials may be used for the substrate and/or dielectric layers, including but not limited to parylene and various combinations of polyimide and silicon carbide (SiC).

The PPy or other polymer coating 124 on the mesh structure may be electrochemically deposited on the Au mesh using a potentiostat, and a variety of coating thicknesses may be used based on their ability to close the mesh gaps in the mesh structure. The coating may additionally and/or alternatively be deposited in any suitable process, such as spin coating directly from the coating solution, spin coating from a precursor or monomer, chemical vapor deposition (CVD), or electrochemical deposition. For example, assuming a reversible 35% strain, PPy may be deposited to a thickness equivalent to ⅔ of half the gap width. The coating thickness depends linearly on the polymerization time, and can be readily adjusted as needed. To improve adhesion of the polymer coating to the mesh structure, the mesh structure may be designed with metal coating the entire 3D structure that allows the polymer coating to wrap completely around. This design may greatly reduce or eliminate the risk of PPy delamination during actuation in physiological fluid. In addition, the electroplating process in fabrication of the mesh structure may leave an inherently rough surface that may reduce or eliminate delamination issues, and the surface and be further roughed using surface modification techniques such as plasma treatment, to further enhance adhesion of the polymer coating to the mesh structure.

The interconnect network 150 is preferably a thin-film structure that is fabricated in the same process as the port gate such that the interconnect network is integrally joined to the port gate. However, alternatively, the interconnect network may be separately fabricated using a similar manufacturing process, and then joined to the port gate. Furthermore, in another alternative, the interconnect network and the plurality of port gates may be separate until they are attached to the fluidic thread, essentially becoming joined only during assembly of the overall neural drug delivery system.

Sensors or electrode sites 160 may be created using any suitable manufacturing process, such as those described in U.S. Patent Application 2006/0282014 entitled "Flexible polymer microelectrodes with delivery capability and methods for making same" or U.S. Patent Application 2008/0208283 entitled "Neural interface system", which are both incorporated in their entirety by this reference, or any other suitable electrode site manufacturing process. In a preferred embodiment, the sensors or electrode sites 160 may include gold, platinum, PPy, or any suitable material. The electrode sites 160 may be patterned directly onto the fluidic thread, onto the interconnect network, and/or separately and later coupled to the fluidic thread and/or interconnect network.

To assemble the neural drug delivery system, the bond pads of the interconnect network are preferably ultrasonically bonded to the connector assembly. The rest of the interconnect network, including the branches, and port gates are preferably attached to the fluidic threads 110 with epoxy or other adhesive, preferably a medical-grade, UV-curable epoxy that is capable of being cured through polyimide, such as Dymax 204-CTH.

During assembly, it is important to accurately place and adhere the interconnect network 150 and port gates 120 to the fluidic thread. In this step, it is critical that the applied epoxy layer used to attach the interconnect network and port gates to the fluidic thread is as thin as possible to avoid clogging the port and/or mesh structure of the port gates. An assembly jig may be used to handle and align the components (e.g. align the sensor or electrode sites, port gates, and/or the ports of the fluidic thread) during this step. A variety of epoxies with different viscosities may also be used to adhere the interconnect network, port gates and/or sensor or electrode array to the fluidic thread. After this attachment step, the mesh structure of the port gates should be well adhered to the fluidic threads and clear of epoxy.

As a person skilled in the art will recognize from the previous detailed description and from the figures and claims, modifications and changes can be made to the preferred embodiments of the invention without departing from the scope of this invention defined in the following claims.

We claim:

1. A neural drug delivery system, which comprises:
 a) at least one fluid delivery conduit comprising a conduit sidewall defining a lumen configured to transport fluid;
 b) at least two fluid delivery ports extending through the conduit sidewall;
 c) a respective port gate supported by the conduit sidewall at each of the at least two fluid delivery ports, each port gate comprising:
  i) a thin-film mesh structure; and
  ii) an electroactive polymer supported by at least a portion of the mesh structure,
 d) wherein each port gate is selectively operable between the following modes:
  i) in the absence of a conductive signal applied to the electroactive polymer, the polymer is stable in an oxidized and expanded state occluding the mesh structure to thereby provide the port gate in a closed mode that prevents transfer of the fluid through the corresponding fluid delivery port; and
  ii) in response to a conductive signal applied to the electroactive polymer, the polymer volumetrically contracts to thereby provide an open mode that allows transfer of the fluid through the fluid delivery port;
 e) a voltage source that provides the conductive signal to the electroactive polymer of the port gates; and
 f) an interconnect network configured to carry the conductive signal to the port gates from the voltage source.

2. The neural drug delivery system of claim 1 wherein the fluid delivery conduit comprises a tube with multiple lumens.

3. The neural drug delivery system of claim 1, further comprising a stylet insertable into the lumen.

4. The neural drug delivery system of claim 1, wherein the at least two fluid delivery ports are arranged at least one of axially along and circumferentially around. the fluid delivery conduit.

5. The neural drug delivery system of claim 1, wherein the port gates supported. by the conduit sidewall at each of the fluid delivery ports further operate in one or more gradient open modes, wherein in each gradient open mode the port gate volumetrically contracts by a discrete amount corresponding to one of a range of conductive signal levels.

6. The neural drug delivery system of claim 1, wherein the electroactive polymer coating is an anion transporting variant of polypyrrole (PPy).

7. The neural drug delivery system of claim 6, wherein the anion transporting variant of polypyrrole (PPy) is characterized as being the product of electropolymerizing polypyrrole in the presence of anions selected from the group consisting of $ClO_4$, $Bf_4$, and $PF_6$.

8. The neural drug delivery system of claim 6, wherein the anion transport variant of polypyttole (PPy) is selected from the group consisting of PPy(C1) gels, PPy($C10_4$) gels reaching approximately 43% strain, PPy($CF_3SO_3$) gels reaching approximately 19% strain, and PPy($PF_6$)reaching approximately 15% strain.

9. The neural drug delivery system of claim 1, wherein the interconnect network includes a central spine arranged along the at least one fluid delivery conduit and one or more branches extending outwardly from the central spine, wherein each branch extends from the central spine to a respective port gate.

10. The neural drug delivery system of claim 9, wherein the central spine of the interconnect network extends axially along the fluid delivery conduit.

11. The neural drug delivery system of claim. 1, further comprising an electrode array that includes an electrode site proximate to one of the at least two fluid delivery ports.

12. The neural drug delivery system of claim 11, wherein the electrode array includes an annular electrode site positioned around a perimeter of at least one of the fluid delivery ports.

13. The neural drug delivery system of claim 11, wherein the electrode array comprises at least one stimulation electrode site.

14. The neural drug delivery system of claim 1, wherein port gates exhibit leakage less than 1 nanoliter/minute in the closed mode.

15. The neural drug delivery system of claim 1, wherein the port gates allow fluid flow of approximately 0.5 to 10 microliters/minute in the open mode.

16. The neural drug delivery system of claim 1, wherein the port gates comprising the electroactive polymer remain stable at 37'C.

17. A neural drug delivery device, which comprises
a) at least one fluid delivery conduit comprising a conduit sidewall defining a lumen configured to transport fluid;
b) at least one fluid delivery port extending through the conduit sidewall; and
c) a port gate supported by the conduit sidewall at the fluid delivery port, the port gate comprising:
  i) a mesh structure; and
  ii) an electroactive polymer supported by at least a portion of the mesh structure,
d) wherein the port gate is selectively operable between the following modes:
  i) in the absence of a conductive signal applied to the electroactive polymer, the polymer is stable in an oxidized and expanded state occluding the mesh structure to thereby provide the port gate in a closed mode that prevents transfer of the fluid through the fluid delivery port; and
  ii) in response to a conductive signal applied to the electroactive polymer, the polymer volumetrically contracts to thereby provide an open mode that allows transfer of the fluid through the fluid delivery port.

18. The neural drug delivery device of claim 17, further including an electrode array including at least one annular stimulation or recording electrode site positioned around a perimeter of the at least one fluid delivery port.

19. The neural drug delivery device of claim 17, wherein the electroactive polymer coating is an anion transporting variant of polypyrrole (PPy).

20. The neural drug delivery device of claim 17, wherein there are at least two fluid delivery ports extending through the conduit sidewall with respective port gates supported by the fluid delivery conduit and wherein a first one of the port gates is operable between the closed and open modes independently of a second port gate.

21. The neural drug delivery device of claim 17, wherein there are at least two fluid delivery conduits with at least one fluid delivery port extending through the respective conduit sidewalls, the delivery ports supporting respective port gates and wherein a first one of the port gates is operable between the closed and open modes independently of a second port gate.

22. The neural drug delivery device of claim 17, wherein the port gate supported by the conduit sidewall at the fluid delivery port further operate in one or more gradient open modes, wherein in each gradient open mode the port gate volumetrically contracts by a discrete amount corresponding to one of a range of conductive signal levels.

23. A neural drug delivery system, which comprises:
a) at least one fluid delivery conduit comprising a conduit sidewall defining a. lumen configured to transport fluid;
b) at least one fluid delivery port extending through the conduit sidewall;
c) a port gate supported by the conduit sidewall at the fluid delivery port, the port gate comprising:
  i) a thin-film mesh structure; and
  ii) an electroactive polymer supported by at least a portion of the mesh structure,
d) wherein the port gate is selectively operable between the following modes:
  i) in the absence of a conductive signal applied to the electroactive polymer, the polymer is stable in an oxidized and expanded state occluding the mesh structure to thereby provide the port gate in a closed. mode that prevents transfer of the fluid through the fluid delivery port;
  ii) in response to a conductive signal being applied to the electroactive polymer, the polymer volumetrically contracts to thereby provide an open mode that allows transfer of the fluid through the fluid delivery port; and
  iii) one or more gradient open modes, wherein in each gradient open mode the port gate volumetrically contracts by a discrete amount corresponding to one of a range of conductive signal levels; and
e) a voltage source that provides the conductive signal to the electroactive polymer of the port gate; and
f) an interconnect network configured to carry the conductive signal to the port gate from the voltage source.

24. The neural drug delivery system of claim 23, wherein the electroactive polymer coating is an anion transporting variant of polypyrrole (PPy).

25. The neural drug delivery system of claim 23, wherein the port gates exhibit leakage less than 1 nanoliter/minute in the closed mode.

26. The neural drug delivery system of claim 23, wherein the port gates allow fluid flow or approximately 0.5 to 10 microliters/minute in the open mode.

27. The neural drug delivery system of claim 23, wherein the port gates comprising the electroactive polymer remain stable at 37° C.

* * * * *

UNITED STATES PATENT AND TRADEMARK OFFICE
CERTIFICATE OF CORRECTION

PATENT NO. : 9,155,861 B2
APPLICATION NO. : 13/236973
DATED : October 13, 2015
INVENTOR(S) : Jamille F. Hetke et al.

It is certified that error appears in the above-identified patent and that said Letters Patent is hereby corrected as shown below:

In the claims,

Column 10, line 51 (Claim 2, line 1) after the words "claim 1" insert a --,--

Column 10, line 57 (Claim 4, line 3) after the word "around" delete the "."

Column 10, line 60 (Claim 5, line 2) after the word "supported" delete the "."

Column 11, line 5 (Claim 7, line 5) delete "Bf4" and insert --BF4--

Column 11, line 8 (Claim 8, line 3) delete "PPy(C10$_4$)" and insert --PPy(ClO4)--

Column 11, line 21 (Claim 11, line 1) after the word "claim" delete the "."

Column 11, line 41 (Claim 17, line 1) after the word "comprises" insert a --:--

Column 12, line 24 (Claim 23, line 3) after the word "a" delete the "."

Column 12, line 37 (Claim 23, line 16) after the word "closed" delete the "."

Signed and Sealed this
Twenty-second Day of March, 2016

Michelle K. Lee
*Director of the United States Patent and Trademark Office*